United States Patent
Balan

(10) Patent No.: US 6,376,718 B1
(45) Date of Patent: Apr. 23, 2002

(54) DEHYDROGENATION OF ALKYLENE GLYCOL ETHERS TO ETHER KETONES AND ALDEHYDES

(75) Inventor: Prakash Balan, Wilmington, DE (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/715,220

(22) Filed: Nov. 17, 2000

(51) Int. Cl.$^7$ ................................................ C07C 45/29
(52) U.S. Cl. ........................ 568/405; 568/383; 568/449; 568/485; 568/486
(58) Field of Search ................ 568/383, 405, 568/485, 486, 449

(56) References Cited

U.S. PATENT DOCUMENTS

| | | | |
|---|---|---|---|
| 3,374,184 A | 3/1968 | McEvoy et al. | 252/467 |
| 3,462,495 A | 8/1969 | Friedli | 260/590 |
| 4,141,919 A | 2/1979 | Gremmelmaier | 260/594 |
| 4,202,808 A | 5/1980 | Fan | 260/29.6 |
| 4,233,246 A | 11/1980 | Dudeck et al. | 568/402 |
| 4,251,396 A | 2/1981 | Frainier et al. | 252/467 |
| 4,431,493 A | 2/1984 | Snoble | 204/79 |
| 4,666,502 A | 5/1987 | Seckinger et al. | 71/90 |
| 5,099,073 A * | 3/1992 | Sanderson et al. | 568/405 |
| 5,576,188 A | 11/1996 | Schlaeppi et al. | 435/7.93 |

FOREIGN PATENT DOCUMENTS

| | | | |
|---|---|---|---|
| CZ | 275182 | 10/1991 | 309/36 |

* cited by examiner

Primary Examiner—Sreeni Padmanabhan
(74) Attorney, Agent, or Firm—Shao Guo

(57) ABSTRACT

A catalytic dehydrogenation of alkylene glycol ether to ether ketone or aldehyde is disclosed. The dehydrogenation is performed with copper chromite catalyst and at least 5 wt % of water based on alkylene glycol ether. It has been found that the selectivity to formation of ether ketone or aldehyde increases with increasing the amount of water in the alkylene glycol ether.

11 Claims, No Drawings

DEHYDROGENATION OF ALKYLENE GLYCOL ETHERS TO ETHER KETONES AND ALDEHYDES

FIELD OF THE INVENTION

The invention relates to the preparation of ether ketones and ether aldehydes. In particular, the invention relates to a catalytic dehydrogenation of alkylene glycol ethers to produce ether ketones and ether aldehydes.

BACKGROUND OF THE INVENTION

Primary alcohols can be converted to aldehydes and secondary alcohols to ketones by dehydrogenation. Similarly, glycol ethers can be converted to ether aldehydes or ether ketones. Catalytic dehydrogenation is more often used industrially because it gives relatively high selectivity to aldehydes or ketones.

U.S. Pat. No. 3,462,495 teaches dehydrogenation of glycol ethers with "calcium nickel phosphate" catalysts. The dehydrogenation is performed by feeding a mixture of glycol ether with from 1 to 25% of water at 425° C. It gives 55% of conversion of glycol ether and 72.5% selectivity to ether ketone.

U.S. Pat. No. 4,233,246 teaches oxidation of glycol ethers to ether ketones with silver/copper metal catalysts in the presence of air. The reaction is carried out in vapor phase by passing glycol ether through multiple layers of catalyst at 450–700° C. While this complicated process gives a high conversion of glycol ether (>99%), it has low selectivity to ether ketone (less than 70%).

U.S. Pat. No. 4,141,919 teaches dehydrogenation of propylene glycol methyl ether in the presence of copper oxide catalyst. The catalyst is treated with hydrogen. A mixture of propylene glycol methyl ether with about 5% of water is passed over the catalyst at about 280° C. It gives less than 50% selectivity to methoxyacetone.

U.S. Pat. No. 4,431,493 teaches electrochemical preparation of ether ketones and ether aldehydes from alkylene glycol ethers. However, the conversion and selectivity are still very low.

A Czech and Slovak patent, C.S. Pat. No. 275,182, also teaches dehydrogenation of propylene glycol methyl ether to methoxyacetone with copper-zinc oxides. The patent discloses that using an aniline derivative in the dehydrogenation can enhance the selectivity to methoxyacetone.

Copending appl. Ser. No. 09/519,398, filed on Mar. 3, 2000, discloses liquid phase oxidation of propylene glycol methyl ether to methoxyacetone using hydrogen peroxide in the presence of a transition metal catalyst. It has achieved a higher conversion and higher selectivity. However, using hydrogen peroxide is inconvenient in a commercial process.

There is an increasing interest in ketones and aldehydes. They are used for making dyes and herbicidal compositions (see, e.g., U.S. Pat. Nos. 4,666,502 and 5,576,188). Ether ketones have found potential uses as co-solvents in water-borne coatings (see, e.g., U.S. Pat. No. 4,202,808). An improved process for making ether ketones and ether aldehydes is thus needed. Ideally, the process would have high selectivity and could be easily commercialized.

SUMMARY OF THE INVENTION

The invention is a process for dehydrogenation of an alkylene glycol ether to an ether ketone or an aldehyde. The process is performed in the presence of a copper chromite catalyst and at least 5 wt % of water based on the amount of alkylene glycol ether. The process gives high selectivity to ketones and aldehydes.

DETAILED DESCRIPTION OF THE INVENTION

The invention is a process for dehydrogenation of alkylene glycol ethers to ether ketones and aldehydes. The process is performed in the presence of a copper chromite catalyst. Suitable copper chromite catalysts can be made by any method known in the art. For example, U.S. Pat No. 3,374,184, the teachings of which are incorporated herein by reference, teaches making copper chromite by reacting cupric nitrate and chromic oxide. In another example, U.S. Pat, No. 4,251,396, the teaching of which are incorporated herein by reference, teaches making copper chromite from copper sulfate and sodium dichromate. Copper chromite catalysts are commercially available, e.g., from Engehard Company. Preferably, the copper chromite for use in the process of the invention contains at least 50 wt % of $CuCr_2O_4$.

The catalyst is preferably treated with hydrogen. Methods for hydrogenation of metal oxides are known. For example, U.S. Pat. No. 4,141,919, the teachings of which are incorporated herein by reference, teaches how to hydrogenate copper oxide. The hydrogenation of copper chromite is exothermic, so hydrogen is added slowly in the beginning and gradually increased when the reaction continues. The hydrogenation is preferably carried out at a temperature from about 125° C. to about 225° C., more preferably from about 150° C. to about 200° C.

The catalyst preferably has a total pore volume within the range of about 0.05 to about 2 cc/g, more preferably from 0.05 to 0.5 cc/g. It preferably has a surface area within the range from about 1 to about 50 m²/g, more preferably from about 5 to about 15 m²/g.

The process of the invention is performed in the presence of at least 5 wt % of water based on alkylene glycol ether. Preferably, the dehydrogenation is performed in the presence of at least 20 wt % of water. More preferably, the process is performed in the presence of at least 40 wt % of water. As shown in the examples, the selectivity to ether ketones increases with increasing water concentration. When about 40 wt % of water is used, the selectivity reaches almost 100%.

Suitable alkylene glycol ethers for use in the dehydrogenation include those having the general structure:

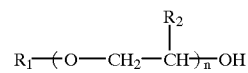

in which $R_1$ is a $C_1$ to $C_{10}$ alkyl group, or a $C_6$ to $C_{10}$ aryl or alkylaryl group, $R_2$ is hydrogen, a $C_1$ to $C_{10}$ alkyl group, or a $C_6$ to $C_{10}$ aryl or alkylaryl group, and n, which is an average number of oxyalkylene units, is within the range of 1 to about 10. Preferably, n is within the range of 1 to about 5. More preferably, n is within the range of 1 to about 3. Preferably, $R_1$ is a $C_1$ to $C_{10}$ alkyl group. More preferably, $R_1$ is a $C_1$ to $C_6$ alkyl group. Preferably, $R_2$ is hydrogen or a $C_1$ to $C_{10}$ alkyl group. More preferably, $R_2$ is hydrogen or methyl group.

Examples of suitable alkylene glycol ethers are propylene glycol methyl ether, propylene glycol n-butyl ether, propylene glycol t-butyl ether, propylene glycol n-propyl ether, dipropylene glycol methyl ether, dipropylene glycol n-butyl ether, dipropylene glycol t-butyl ether, dipropylene glycol n-propyl ether, tripropylene glycol methyl ether, ethylene glycol methyl ether, ethylene glycol n-butyl ether, diethylene glycol methyl ether, diethylene glycol n-propyl ether, and the like, and mixtures thereof.

The dehydrogenation converts primary hydroxyl group of alkylene glycol ether to aldehyde and secondary hydroxyl group to ketone. For example, dehydrogenation of propylene glycol methyl ether gives methoxyacetone, while the dehydrogenation of ethylene glycol methyl ether gives methoxyformaldehyde. Ether ketones and aldehydes prepared by the hydrogenation of the invention include those represented by the formula:

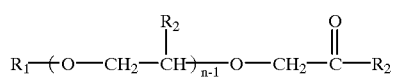

$R_1$, $R_2$ and n are defined above.

The process is preferably performed at a temperature within the range of about 150° C. to about 350° C. More preferably, the process is performed at a temperature within the range of about 220° C. to about 280° C.

The following examples merely illustrate the invention. Those skilled in the art will recognize many variations that are within the spirit of the invention and scope of the claims.

EXAMPLE 1

The hydrogenation is carried out in a stainless steel fixed bed reactor. Copper chromite catalyst (4.1 kg, Cu-0203-T, product of Engelhard Company) is loaded into the reactor. The catalyst is activated using a mixture of hydrogen and nitrogen. To drive out moisture and air, the catalyst bed is heated to 150° C. and remains at this temperature for 5–8 hours under nitrogen flow in a rate of 500 1/hr. Hydrogen is then added into the reactor. The reaction is exothermic, so hydrogen is added slowly in the beginning in a rate that is 1.0–1.5% of the nitrogen flow rate. As the reaction continues, hydrogen concentration is gradually increased so as to control the temperature not to exceed 170° C. At the end of the reaction, hydrogen concentration reaches 100%.

A mixture of 40 wt % water and 60 wt % of propylene glycol methyl ether is fed into the reactor at a weight-hourly space-velocity (WHSV) of 1.1. Reactor temperature is maintained at 250° C. In the steady state, the conversion of propylene glycol methyl ether is 43.5% and selectivity to methoxyacetone is 95.2 mole %.

EXAMPLE 2

Example 1 is repeated, but a mixture of 20 wt % water and 80 wt % propylene glycol methyl ether is used. In the steady state, the conversion of propylene glycol methyl ether is 37.5% and selectivity to methoxyacetone is 85.4 mole %.

EXAMPLE 3

Example 1 is repeated, but a mixture of 10 wt % water and 90 wt % propylene glycol methyl ether is used. In the steady state, the conversion of propylene glycol methyl ether is 34% and selectivity to methoxyacetone is 75.2 mole %.

EXAMPLE 4

Example 1 is repeated but a mixture of 5 wt % water and 95 wt % propylene glycol methyl ether is used. In the steady state, the conversion of propylene glycol methyl ether is 39.0% and selectivity to methoxyacetone is 64 mole %.

COMPARATIVE EXAMPLE 5

Example 1 is repeated, but pure propylene glycol methyl ether is used. In the steady state, the conversion of propylene glycol methyl ether is 56% and selectivity to methoxyacetone is 37%.

EXAMPLE 6

Example 1 is repeated, but the dehydrogenation is conducted at 280° C. In the steady state, the conversion of propylene glycol methyl ether is 76% and selectivity to methoxyacetone is 99%.

COMPARATIVE EXAMPLE 7

Example 6 is repeated, but pure propylene glycol methyl ether is used. In the steady state, the conversion of propylene glycol methyl ether is 65% and selectivity to methoxyacetone is 71%.

I claim:

1. A process which comprises dehydrogenating an alkylene glycol ether to an ether ketone or an ether aldehyde, wherein the process is performed in the presence of a copper chromite catalyst and at least 5 wt % of water, based on the amount of alkylene glycol ether.

2. The process of claim 1 wherein the copper chromite catalyst contains at least 50 wt % of $CuCr_2O_4$.

3. The process of claim 1 wherein the copper chromite catalyst is hydrogenated.

4. The process of claim 1 wherein the alkylene glycol ether has the structure:

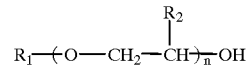

in which $R_1$ is a $C_1$ to $C_{10}$ alkyl group, or a $C_6$ to $C_{10}$ aryl or alkylaryl group, $R_2$ is hydrogen, a $C_1$ to $C_{10}$ alkyl group, or a $C_6$ to $C_{10}$ aryl or alkylaryl group, and n, which is an average number of oxyalkylene units, is within the range of 1 to about 10.

5. The process of claim 1 performed at a temperature within the range of about 150° C. to about 350° C.

6. The process of claim 1 performed at a temperature within the range of about 220° C. to about 280° C.

7. The process of claim 1 wherein the alkylene glycol ether is selected from the group consisting of propylene glycol alkyl ethers, ethylene glycol alkyl ethers, butylene glycol alkyl ethers, and mixtures thereof.

8. The process of claim 1 wherein the alkylene glycol ether is a propylene glycol methyl ether.

9. The process of claim 1 performed in the presence of at least 20 wt % of water based on the amount of alkylene glycol ether.

10. The process of claim 1 performed in the presence of at least 40 wt % of water based on the amount of alkylene glycol ether.

11. A process comprising dehydrogenating propylene glycol methyl ether to produce methoxyacetone, wherein the process is performed in the presence of a copper chromite that contains at least 50 wt % of $CuCr_2O_4$ and in the presence of at least 40 wt % of water based on the amount of propylene glycol methyl ether.

* * * * *